United States Patent

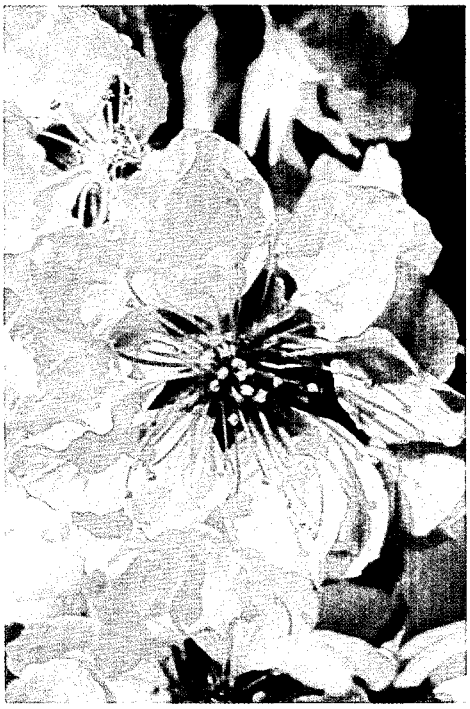
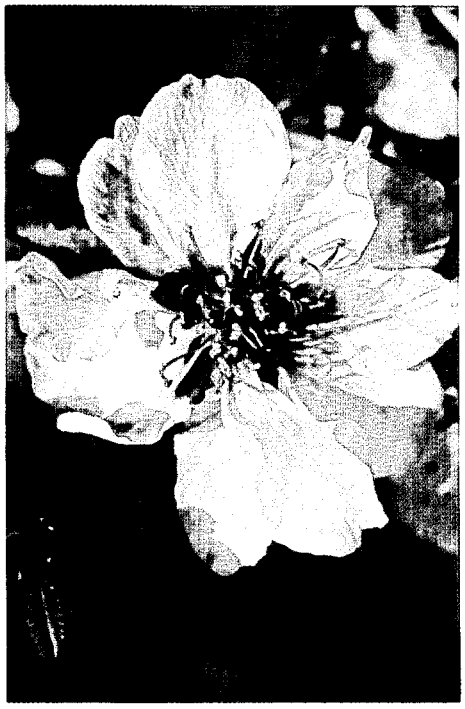
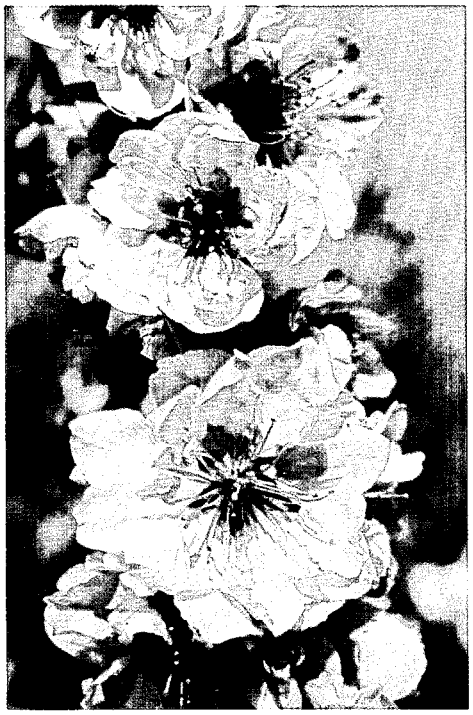
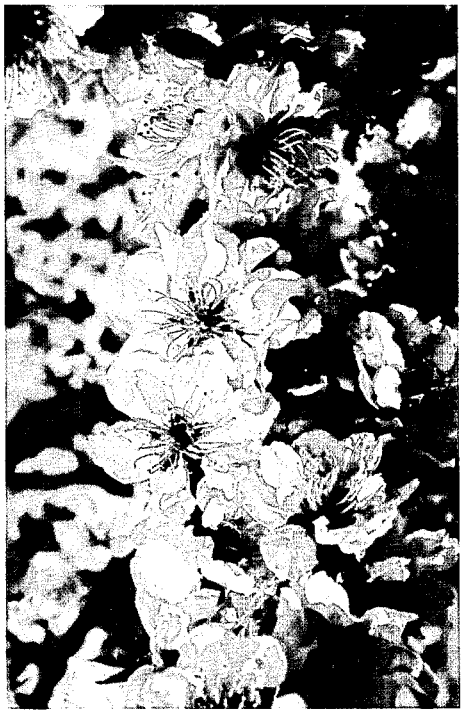

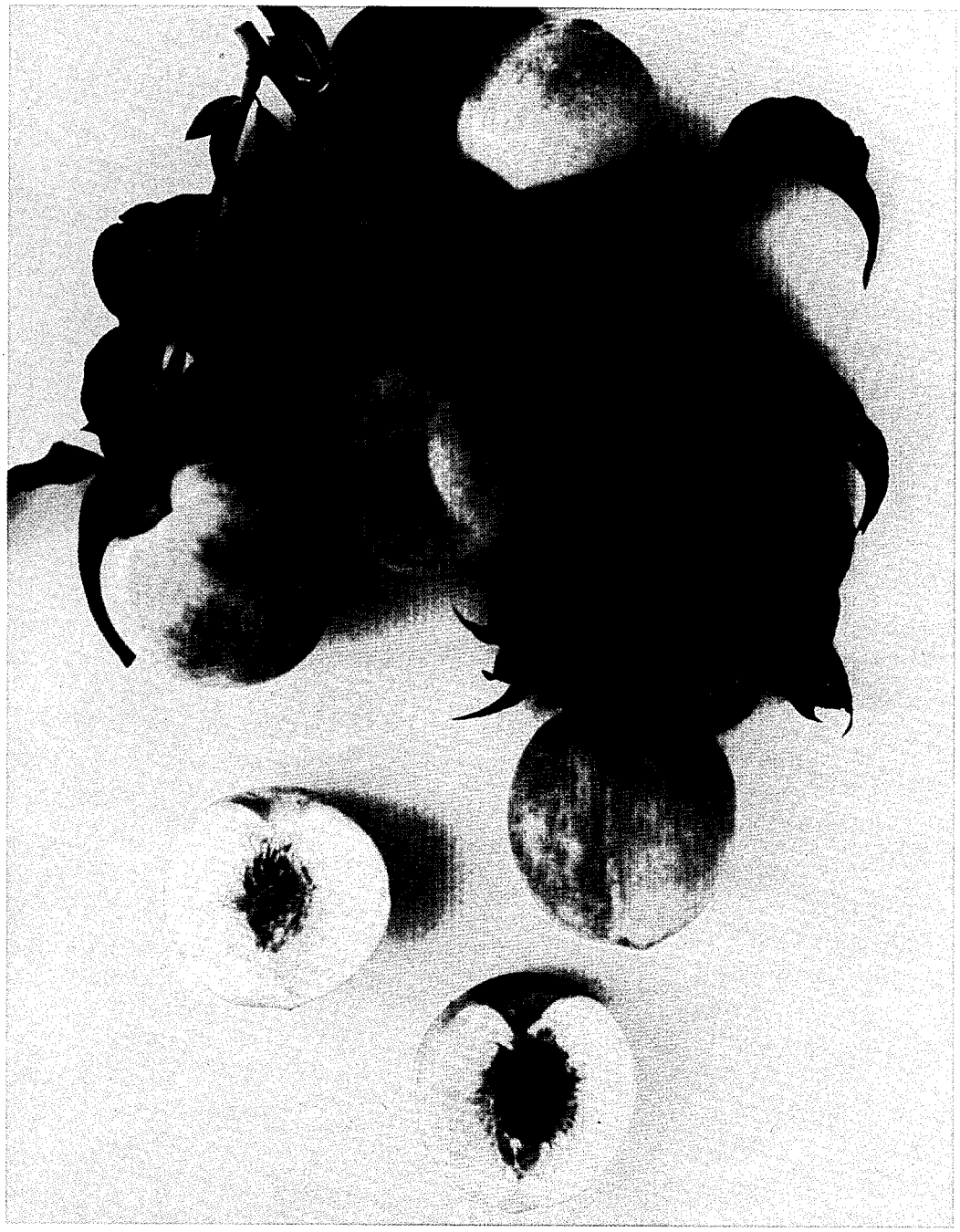

Plant Pat. 3,806

Patented Nov. 18, 1975

3,806

PEACH TREE

Merle M. Fountain, 1148 Meikle Road,
Hickman, Calif. 95323

Filed Nov. 25, 1974, Ser. No. 527,163

Int. Cl. A01h 5/03

U.S. Cl. Plt.—43 1 Claim

ABSTRACT OF THE DISCLOSURE

A peach tree of medium size and vigor, spreading, dense, vase-formed, heavily foliated with large lanceolate leaves, blooming profusely with large, pink, double, ruffled flowers, and a regular and very productive bearer of medium size, uniform, globose, freestone fruit of good eating quality; the fruit—which ripens in mid-season—having yellow skin with substantial overspreading with red, and yellow flesh partially streaked and mottled with red.

BACKGROUND OF THE VARIETY

As an orchardist, it is my practice to maintain a continuing observation (by recurrent inspection) of the fruit trees growing on my ranch located near Hickman, Stanislaus County, Calif., and—during the course of such an inspection—I discovered the present variety of peach tree.

ORIGIN OF THE VARIETY

The present variety of peach tree was discovered by me growing as a limb mutation on a Fay Elberta (unpatented) peach tree in my orchard located as aforesaid; the discovery having been made at a time when the mutation limb was blooming, and at which time I recognized that the flowers were new and distinct in comparison to those of conventional varieties of peach trees. With my attention thus drawn to the mutation limb, I later observed it and found it bore medium size, yellow flesh, freestone fruit of good eating quality. I, therefore, determined to asexually reproduce the variety represented by such mutation limb.

ASEXUAL REPRODUCTION OF THE VARIETY

The present variety of peach tree was asexually reproduced, on my behalf by a commercial nursery, by budding onto conventional rootstock at growing grounds located near Hickman, Stanislaus County, Calif., and—in maturity—such reproductions ran true to the original mutation limb in all respects.

SUMMARY OF THE VARIETY

The present variety of peach tree is distinctively characterized, in summary, by blooming profusely with pink, highly visually attractive, double, ruffled flowers; and by bearing medium size, yellow flesh, freestone fruit of good eating quality. The tree of the present variety presents—when in full bloom—a beautiful flower display not common to conventional varieties of commercially grown peach trees, but more in the fashion of an ornamental.

BRIEF DESCRIPTION OF THE DRAWINGS

The drawings (in two sheets) are illustrations, by photographic reproductions in color, showing—on one sheet—a series of photographs of flowers of the variety, and—on a second sheet—depicting a twig with leaves and attached fruit, together with separate fruit, one of the latter being cut in half to expose the flesh, with the stone remaining in one of the halves.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Vigor.*—Medium.
- *Growth.*—Spreading.
- *Density.*—Dense.
- *Form.*—Vase-formed.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Gray-green.

Lenticels:
- *Number.*—Numerious.
- *Size.*—Medium.

Leaves:
- *Size.*—Large. Average length—4"–5½". Average width—1"–1½".
- *Form.*—Lanceolate.
- *Margin.*—Finely serrate.
- *Petiole.*—Medium length. Medium thickness.
- *Glands.*—Average number—2. Alternate. Small. Globose. Green.
- *Stipules.*—None.
- *Color.*—Top side—Medium green (24–L–8). Under side—Lighter green (22–G–7).

Flower buds:
- *Hardiness.*—Hardy.
- *Size.*—Large.
- *Form.*—Plump. Free.

Flowers:
- *Blooming period.*—Date of first bloom—Mar. 1, 1974. Date of full bloom.—Mar. 12, 1974. Date of petal fall.—Mar. 24, 1974. Medium, as compared with other varieties.
- *Size.*—Large.
- *Quantity.*—Profuse.
- *Color.*—Pink.
- *Form.*—Double, ruffled in full bloom; i.e., an inner row of flat petals, and a double row of smaller superposed petals mainly ruffled.

Fruit:
- *Maturity when described.*—Eating ripe—Aug. 12, 1974.
- *Date of first picking.*—Aug. 8, 1974.
- *Date of last picking.*—Aug. 12, 1974.
- *Size.*—Uniform. Medium. Average diameter axially—2½". Average weight per peach—0.434 lb.
- *Form.*—Uniform. Globose.
- *Suture.*—An inconspicuous line.
- *Ventral surface.*—Rounded slightly.
- *Cavity.*—Rounded.
- *Base.*—Truncate.
- *Apex.*—Short.

Skin:
- *Texture.*—Medium.
- *Tendency to crack.*—None in dry season.
- *Down.*—Moderate. Medium length.
- *Color.*—Yellow (11–L–5), with substantial overspreading with red (5–L–7) shading to darker red (7–L–7).

Flesh:
- *Amygdalin.*—Scant.
- *Juice.*—Abundant.
- *Texture.*—Firm.
- *Fibers.*—Few.

*Ripens.*—Evenly.
*Flavor.*—Mild.
*Aroma.*—Distinct.
*Eating quality.*—Good.
*Color.*—Yellow (10–K–5) partially streaked and mottled with red (7–L–6). Surface of pit cavity. Red (7–L–6) with yellow fibers.

Stone:
*Type.*—Free.
*Size.*—Medium. Average length—1¼″. Average breadth—¾″. Average thickness—⅝″.
*Color.*—Brown (8–J–10).

Use: Dessert. Canning. Freezing. Drying. Superior to many commercial peach varieties, including Fay Elberta, grown for the above purposes.
Keeping quality: Good.
Shipping quality: Good.
Resistance to insects: Good.
Resistance to diseases: Medium.

Because of its distinctive characteristics (i.e., the exceptionally visually attractive flowers at blooming, together with the bearing of medium size, yellow flesh, freestone fruit of good eating quality, the variety is exceptionally well suited for growing in a garden or family orchard, yet may also find substantial acceptance for commerical orchard production.

The tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, characterized by blooming profusely with large, pink, double, ruffled flowers, and bearing regularly and productively medium size, uniform, globose, freestone fruit having yellow skin with substantial overspreading of red, and yellow flesh partially streaked and mottled with red.

No references cited.

ROBERT E. BAGWILL, Primary Examiner